United States Patent [19]
Baker et al.

[11] Patent Number: 5,817,841
[45] Date of Patent: Oct. 6, 1998

[54] MEMBRANE PROCESS FOR ARGON PURGING FROM ETHYLENE OXIDE REACTORS

[75] Inventors: Richard W. Baker, Palo Alto, Calif.; Shannon Goakey, Hillsboro, Oreg.; Douglas Gottschlich, Mountain View, Calif.

[73] Assignee: Membrane Technology and Research, Inc., Menlo Park, Calif.

[21] Appl. No.: 890,856

[22] Filed: Jul. 10, 1997

[51] Int. Cl.$^6$ .................................................. C07D 303/00
[52] U.S. Cl. ............................................................... 549/513
[58] Field of Search .............................................. 549/513

[56] References Cited

U.S. PATENT DOCUMENTS

| | | | |
|---|---|---|---|
| 4,553,983 | 11/1985 | Baker | 55/16 |
| 4,685,940 | 8/1987 | Soffer et al. | 557/158 |
| 4,857,078 | 8/1989 | Watler | 55/15 |
| 4,879,396 | 11/1989 | Ozero | 549/534 |
| 4,904,807 | 2/1990 | Ozero | 549/534 |
| 4,906,256 | 3/1990 | Baker et al. | 55/16 |
| 4,963,165 | 10/1990 | Blume et al. | 55/16 |
| 4,994,094 | 2/1991 | Behling et al. | 55/16 |
| 5,032,148 | 7/1991 | Baker et al. | 55/16 |
| 5,044,166 | 9/1991 | Wijmans et al. | 62/65 |
| 5,069,686 | 12/1991 | Baker et al. | 55/16 |
| 5,127,926 | 7/1992 | Baker et al. | 55/16 |
| 5,281,255 | 1/1994 | Toy et al. | 95/50 |
| 5,332,424 | 7/1994 | Rao et al. | 95/47 |
| 5,501,722 | 3/1996 | Toy et al. | 95/50 |

OTHER PUBLICATIONS

R.W. Baker, J. Kaschemekat, J.G. Wijmans, "Membrane Systems for Profitable VOC Recovery," CHEMTECH, Jul. 1996.

R.W. Baker, M. Jacobs, "Improve Monomer Recovery from Polyolefin Resin Degassing," Hydrocarbon Processing, Mar. 1996.

*Primary Examiner*—John Kight
*Assistant Examiner*—Garth M. Dahlen
*Attorney, Agent, or Firm*—J. Farrant

[57] ABSTRACT

A process and apparatus for ethylene oxide production. A membrane unit containing a membrane selectively permeable to ethylene over argon is used to recover ethylene from the argon purge stream.

16 Claims, 7 Drawing Sheets

5,817,841

MEMBRANE PROCESS FOR ARGON PURGING FROM ETHYLENE OXIDE REACTORS

FIELD OF THE INVENTION

The invention relates to manufacture of ethylene oxide in a reactor, and in particular to using a membrane unit to treat off-gas streams from the reactor to purge argon gas without losing large amounts of ethylene reagent.

BACKGROUND OF THE INVENTION

A large number of chemical intermediates are produced by catalytic oxidation of an appropriate hydrocarbon feedstock. One of the most important intermediates produced in this manner is ethylene oxide, which is made by oxidation of ethylene in the presence of a silver catalyst. The process operates in a loop, with modest conversion per pass, so that large amounts of ethylene are recirculated back to the reactor at each pass. The raw gas from the reactor is usually scrubbed with water to remove the ethylene oxide product before the gas is recirculated.

Many oxidation processes were originally developed using air as the oxygen source, but modern processes more commonly operate with a feed of high-purity oxygen. The use of pure oxygen typically increases yields and reduces or eliminates the need for nitrogen purging from the process loop, since much less inert gas is fed into the loop initially.

Even when oxygen-oxidation is used, however, some purging is necessary. This is because "pure" oxygen is typically slightly less than 100% pure. The most significant other component is argon, with a typical concentration of about 1%. Argon is present in air and, since argon and oxygen have close boiling points, is not well separated in the cryogenic distillation process used to produce oxygen from air.

If argon is not removed, it builds up in the ethylene oxide reactor loop, and can adversely affect the reaction dynamics and the flammability of the gas mixture, and/or reduce the life of the catalyst. Therefore, ethylene oxide production processes normally provide for a small purge stream to be withdrawn from the loop, usually after the ethylene oxide product has been scrubbed out. In addition to argon, the purge gas typically contains unreacted ethylene and oxygen; carbon dioxide (produced in a side reaction in which ethylene is fully oxidized); methane, which is added to the reactor to control the flammability of the gas mixture; nitrogen; and small amounts of ethane and other contaminants. In prior art processes, this stream is incinerated or used as boiler fuel.

Although the volume of the purge stream is small, its destruction results in the loss, from a typical plant, of about 16 lb of ethylene for every ton of ethylene oxide produced. At current estimated U.S. annual production of $7.75 \times 10^9$ lb, this represents a feedstock loss of about 60 million lb, or worldwide perhaps three times that amount. In a large-scale process of this type, even incremental improvements in efficiency can affect process economics significantly. Therefore, a process that can reduce or eliminate this loss of ethylene feedstock would be valuable to the industry.

Separation of certain gas mixtures by means of selective membranes has been known to be possible for many years, and membrane-based gas separation systems are emerging to challenge conventional separations technology in a number of areas. That membranes have the potential to separate organic vapors from other gases is also known. For example, U.S. Pat. Nos. 4,553,983; 4,857,078; 4,963,165; 4,906,256; 4,994,094; 5,032,148; 5,069,686; 5,127,926; 5,281,255 and 5,501,722 all describe membranes, systems or processes suitable for such separations.

U.S. Pat. No. 4,879,396, to Ozero, discloses a process for removing both carbon dioxide and argon from an ethylene oxide reactor loop by means of an argon-selective membrane, that is, a membrane that preferentially permeates argon and retains ethylene. U.S. Pat. No. 4,904,807, also to Ozero, discloses a process for removing argon from the reactor loop by means of an argon-selective membrane. In both cases, because the membrane is not perfectly selective, a portion of the ethylene is lost inevitably with the argon vent stream.

SUMMARY OF THE INVENTION

The invention is a process and apparatus for producing ethylene oxide that provides a new and advantageous technique for venting excess argon from the reaction loop with reduced loss of ethylene.

In its basic form, the process of the invention comprises:
(a) reacting ethylene and oxygen in a reaction zone to form ethylene oxide;
(b) withdrawing from the reaction zone a product stream comprising ethylene oxide, ethylene and argon;
(c) removing at least a portion of the ethylene oxide from the product stream to form a non-product stream;
(d) providing a membrane having a feed side and a permeate side, and being selectively permeable to ethylene over argon;
(e) passing at least a portion of the non-product stream across the feed side under conditions in which there is a pressure drop from the feed side to the permeate side;
(f) withdrawing from the feed side an argon-rich purge stream enriched in argon and depleted in ethylene compared with the non-product stream;
(g) withdrawing from the permeate side an ethylene-rich permeate stream enriched in ethylene and depleted in argon compared with the non-product stream;
(h) recirculating at least a portion of the ethylene-rich permeate stream to the reaction zone; the process being characterized by a stage-cut between the ethylene-rich permeate stream and the non-product stream of at least about 30%.

Step (a), the reaction of ethylene and oxygen to form ethylene oxide may be carried out in any known manner, such as by using an air-oxidation process or an oxygen-oxidation process in the presence of a silver catalyst. The reaction may be carried out in a single reaction step or in multiple reaction steps. Depending on the specifics of the reaction process used, the gas mixture withdrawn from the reactor typically contains ethylene oxide, ethylene, oxygen, ethane, carbon dioxide, nitrogen, methane, argon, water vapor and minor amounts of other components. If an air-oxidation process is used, the gas will obviously contain large amounts of nitrogen; if an oxygen-oxidation process is used, methane is added to raise the flammability limit of the feed gas and can be present in large quantities in the off-gas.

The ethylene oxide may be removed from the raw gas exiting the reactor, as specified in step (c), by any convenient technique. The standard procedure in the industry is to absorb the ethylene oxide into water, leaving a scrubbed gas stream. In prior art processes, a small amount of this scrubbed gas stream is purged to remove argon, as explained in the background section above. The remainder, or at least a portion of the remainder, is further treated to remove carbon dioxide, and then recirculated to the reactor.

In the process of the invention, a portion of the scrubbed non-product gas stream is passed to a membrane unit. The unit contains a membrane, preferably a rubbery membrane, that is selectively permeable to ethylene compared with argon; that is, it permeates ethylene faster than argon.

The membrane separation process may be configured in many ways, and may include a single bank of membrane modules or an array of two or more banks in multi-stage or multi-step arrangements.

A driving force for permeation across the membrane is usually provided by maintaining a pressure difference between the feed and permeate sides. This can be accomplished in a variety of ways.

Since the membrane is selectively permeable to ethylene, the residue stream leaving the feed side of the membrane is enriched in argon and depleted in ethylene compared with the feed stream to the membrane. It is possible to remove from the membrane feed stream, that is, to recover into the membrane permeate stream, a chosen percentage, such as 30%, 40%, 50%, 60%, 70%, 80%, 90%, 95% or even 99% of the ethylene that would otherwise be vented and lost. The amount of ethylene removed can be controlled by varying the stage cut at which the membrane unit operates, as explained in the Detailed Description below. To achieve good ethylene recovery, it is preferred that the membrane unit be operated at a stage-cut of at least about 30%, more preferably at least about 50% and most preferably higher. Thus, the residue stream can be vented to control argon content in the reactor with little loss of ethylene. The ethylene, which has been captured in the permeate stream, may be recirculated to the reactor.

As in prior art processes, carbon dioxide as well as argon must be removed from the reactor off-gas to control build-up in the reactor. This may be done by any convenient method.

The carbon dioxide removal step may be carried out on a separate portion of the scrubbed, non-product gas stream, may be carried out on the permeate stream following the removal of argon by the membrane separation step, or may be carried out upstream of the membrane separation step, for example. This flexibility represents a further advantage of the invention. Since it is generally, although not necessarily, the case that the ethylene-enriched stream will be returned to the reactor loop, this recirculation of part of a stream that was previously vented from the loop can be used to adjust the reaction characteristics to some extent.

In another aspect, the invention is apparatus for ethylene oxide manufacture, including a reactor, an ethylene oxide recovery train, a carbon dioxide removal unit and a membrane unit, containing a membrane selectively permeable to ethylene over argon, for argon removal.

In yet another aspect, the invention is a process for treating an argon purge stream to vent argon and recapture ethylene.

It is an object of the invention to improve ethylene oxide manufacturing processes.

It is an object of the invention to provide a process for removing argon from ethylene oxide reactor vent streams.

It is an object of the invention to provide a process for removing argon from ethylene oxide reactor vent streams with minimal corresponding loss of ethylene.

Other objects and advantages of the invention will be apparent from the description of the invention to those of ordinary skill in the art.

DETAILED DESCRIPTION OF THE INVENTION

Figure 1:
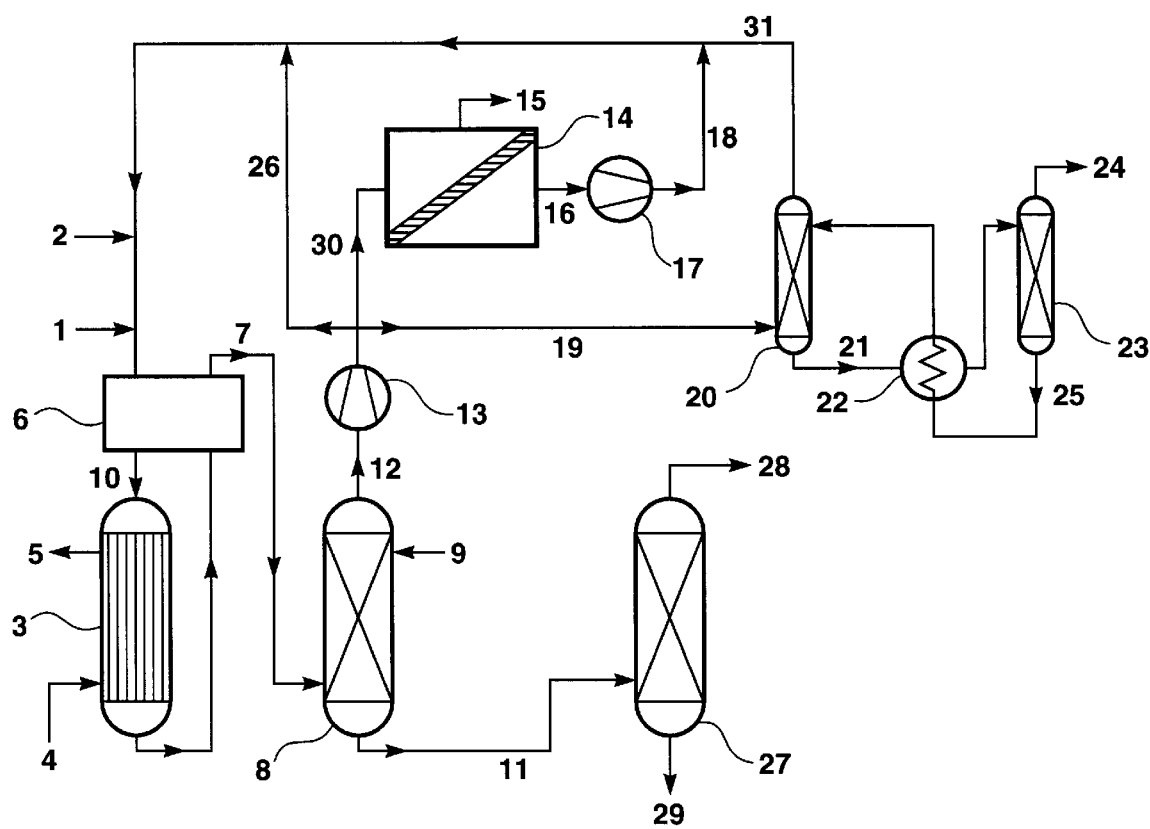
FIG. 1 is a schematic diagram of an ethylene oxide production process in which a purge stream is withdrawn from the reactor loop and treated by membrane separation to remove argon.

The term stage-cut as used herein means the ratio of the membrane permeate volume flow to the membrane feed volume flow.

The term rubbery as used herein means rubbery or elastomeric.

The terms two-step and multi-step mean an arrangement of membrane modules or banks of modules connected together such that the residue stream from one module or bank of modules becomes the feedstream for the next.

The term two-stage and multi-stage mean an arrangement of membrane modules or banks of modules connected together such that the permeate stream from one module or bank of modules becomes the feedstream for the next.

The term membrane array means a set of membrane modules or banks of modules connected in a multi-step arrangement, a multi-stage arrangement, or mixtures or combinations of these.

The term product residue stream means the residue stream exiting a membrane array when the membrane separation process is complete. This stream may be derived from one membrane bank, or may be the pooled residue streams from several membrane banks.

The term product permeate stream means the permeate stream exiting a membrane array when the membrane separation process is complete. This stream may be derived from one membrane bank, or may be the pooled permeate streams from several membrane banks.

All percentages cited herein are by volume unless specifically stated otherwise.

In a basic embodiment, the process of the invention includes the following steps:

1. Reaction of ethylene and oxygen to make ethylene oxide.
2. Treatment of gas exiting the reactor to separate ethylene oxide, and subsequent recovery of ethylene oxide product.
3. Argon removal from the reactor recirculation loop.
4. Carbon dioxide removal from the reactor recirculation loop.
5. Recirculation of unreacted reagents to the reactor.

Operation of ethylene oxide reactors is well known in the art, and is described, for example, in U.S. Pat. Nos. 4,904, 807 and 4,879,396, to Ozero, both incorporated herein by reference, and in "Air Pollution Engineering Manual", A. J. Buonicore and W. T. Davis (Eds), pages 422–432, Van Nostrand Reinhold, New York, 1992.

In the process of the invention, steps 1 and 2, reaction and ethylene oxide separation, can be carried out by any known techniques. Ethylene oxide is formed from ethylene and oxygen by the reaction:

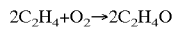

$$2C_2H_4 + O_2 \rightarrow 2C_2H_4O$$

Modern reactors perform this reaction in the vapor phase and in the presence of a silver catalyst at temperatures typically up to 400° C. and pressures typically up to 500 psia. Under these conditions, a secondary reaction:

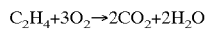

$$C_2H_4 + 3O_2 \rightarrow 2CO_2 + 2H_2O$$

in which ethylene is fully oxidized to carbon dioxide, also occurs to a limited extent.

If an air-oxidation process is used, the reaction is preferably carried out in two or more stages. The reaction mixture, consisting of recirculated and fresh gas, enters the primary reactor, where partial conversion of ethylene to ethylene oxide occurs. The reacted mixture is withdrawn from the reactor and passed to the primary absorber, where ethylene oxide is scrubbed out into water. The scrubbed gas is divided into two portions, one of which is returned to the primary reactor, and the other is passed to the purge reactor or series of reactors. The purge reactor converts most of the ethylene remaining in the purge stream. After ethylene oxide removal, gas exiting the purge reactor is likewise divided into portions, for direct return to the purge reactor, and for treatment to remove excess inert gases.

If an oxygen-oxidation process is used, the reaction is preferably accomplished in one stage, that is, without a purge reactor, as this will generally result in higher conversion of ethylene to ethylene oxide, rather than carbon dioxide. In this case, the gas exiting the reactor can be split into a direct recycle stream and into a portion or portions that are sent for inerts removal.

The reactors themselves may be of any kind that provide for good contact between reagents and catalyst and for good temperature control and removal of waste heat. Shell and tube reactors, with the catalyst on the inner surfaces of the tubes and a coolant, such as water, flowing on the shell side, are preferred.

The exact composition of the reaction mixture may be varied in conjunction with pressure, temperature and flow rate to provide a desired overall yield, efficiency per pass and so on, as is known in the art. As a guideline, the reaction mixture will typically contain, on a percentage basis, between about 10 and 50 moles of total reagents, that is, ethylene and oxygen, up to about 60 moles of inerts, that is methane and nitrogen, and up to around 40 moles total of carbon dioxide and argon. In general, the methane/nitrogen inerts are kept at a high level, such as at least 50% of the mixture, and even such as 55% or 60%, to avoid forming potentially explosive ethylene/oxygen mixtures, as well as to suppress the carbon-dioxide-forming, full oxidation reaction.

The reaction may be carried out at pressures up to 500 psia or above. However, very high pressures are not necessary and a pressure in the range 150–450 psia is generally preferred. At high temperatures, the yield of ethylene oxide diminishes, so preferred operating temperatures are below 400° C., and most preferably around 250° C., such as 200–300° C.

Separation and recovery of the ethylene oxide from the raw gas exiting the reactor can be performed by any known method. For example, the raw gas can be passed into a scrubbing column and run counter-current to a water stream. Ethylene oxide is readily absorbed into the water to form a dilute aqueous solution. The solution can then be passed to a recovery train, including, for example, one or more stripping columns and distillation units, such as is known in the art, for purification and retrieval of the ethylene oxide product.

Steps 3 and 4, purging of argon and carbon dioxide from the reactor loop, represent an important aspect of the invention. In particular, the manner in which the argon purging is carried out differs from the prior art.

As was mentioned in the Background section above, current processes withdraw a stream of sufficient volume to maintain an acceptable argon concentration, and burn it as fuel or simply incinerate it. Since this stream often contains two or three times as much ethylene as argon, this means that 2–3 moles of ethylene may be lost for every mole of argon that is purged. The processes of the invention, on the other hand, are able to recover and recirculate significant amounts, typically 30% or more, such as 40%, 50%, 60%, 70%, 80%, 90%, 95% or even more of the ethylene content of this argon purge stream. That is, as a specific example, if the argon purge stream contains 3 moles of ethylene per mole of argon, use of the process of the invention can reduce the ethylene loss from 3 moles/mole of argon to 2.1 moles/mole of argon, 1.8 moles/mole of argon, 1.5 moles/mole of argon, 1.2 moles/mole of argon, 0.9 moles/mole of argon, 0.6 moles/mole of argon, 0.3 moles/mole of argon, 0.15 moles/mole of argon or even less.

Figure 2:
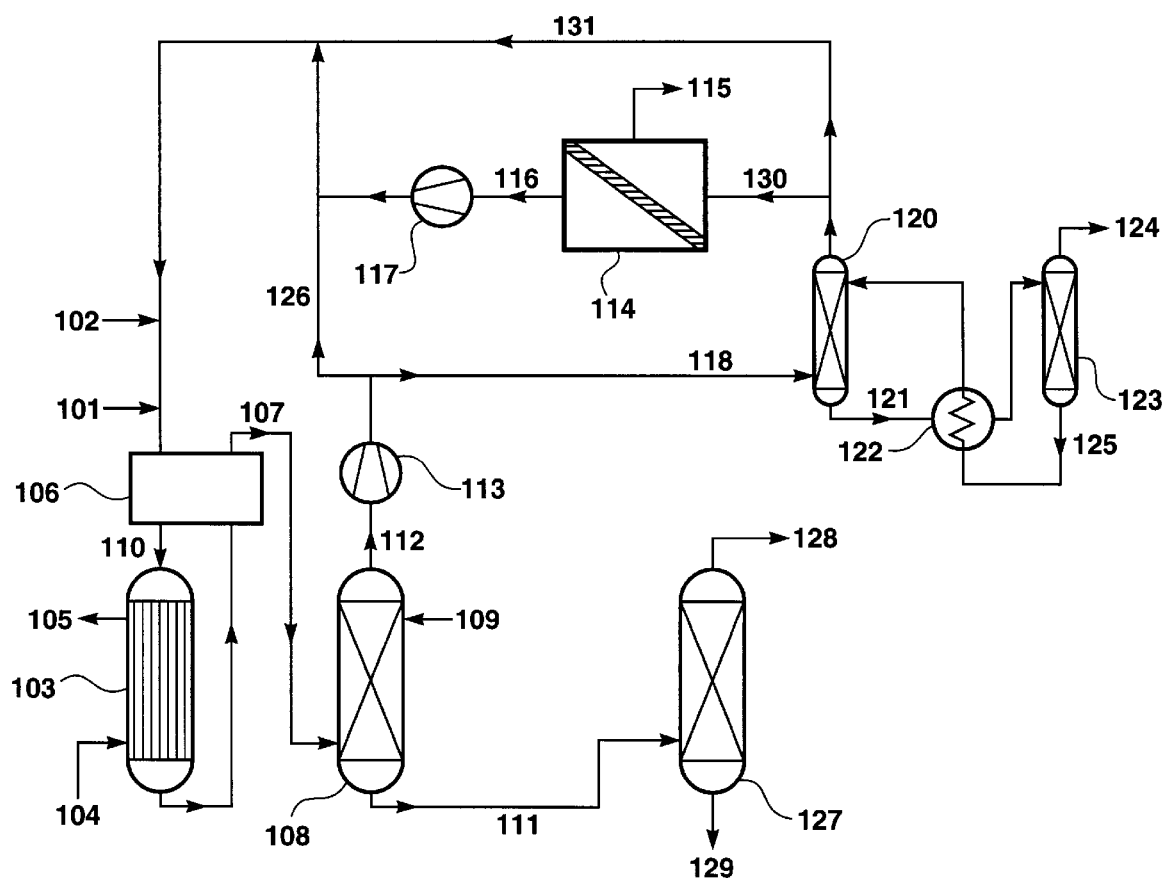
FIG. 2 is a schematic diagram of an ethylene oxide production process in which a membrane unit is incorporated into the reactor loop to remove argon following carbon dioxide removal.

Various process configurations for achieving this result are possible within the scope of the invention. FIGS. 1 and 2 show two representative, but nonlimiting, embodiments of the invention. It will be appreciated by those of skill in the art that these are very simple schematic diagrams, intended to make clear the key aspects of the invention, and that an actual process train will usually include many additional components of a standard type, such as heaters, chillers, condensers, pumps, blowers, other types of separation and/or fractionation equipment, valves, switches, controllers, pressure-, temperature-, level- and flow-measuring devices and the like.

Turning now to FIG. 1, ethylene, stream 1, and oxygen, stream 2, enter the process and are mixed with recirculating gas, 31. The stream passes through heat exchanger 6 and enters reactor 3 as feed stream 10. The reactor is cooled by passing water in at line 4 and withdrawing steam at line 5. Gas containing the newly formed ethylene oxide exits the reactor as stream 7, is cooled by heat exchange against incoming stream 10, and passes to absorber 8. Water enters the absorber as stream 9; an aqueous solution of ethylene oxide is withdrawn as stream 11 and passes to a purification train, indicated as column 27. Ethylene oxide product is withdrawn as stream 28; water and any remaining contaminants are withdrawn as stream 29.

The overhead stream 12 from the ethylene oxide absorber contains a mixture of ethylene, oxygen, carbon dioxide, nitrogen, argon, methane and trace amounts of other gases. The proportions of the component gases in the mix vary, depending on the specific reaction conditions. Typical values for an oxygen-oxidation reactor are in the range up to 40% ethylene, up to 10% oxygen, up to 10% carbon dioxide, a few percent nitrogen, up to 20% argon and up to 60% methane. This stream is recompressed in compressor 13 and split into three portions.

Stream 26 joins with stream 31 for recirculation to the reactor. Stream 19 is treated to remove excess carbon dioxide by any known method. In the representative embodiment of the figure, stream 19 passes to scrubbing column 20. A scrubbing solution, such as hot potassium carbonate, enters the scrubber as stream 25 and exits as stream 21 loaded with carbon dioxide. Stream 21 passes through heat exchanger 22 where it is cooled by flowing against incoming stream 25. Stream 21 is then stripped or otherwise regenerated in unit 23, and waste carbon dioxide is vented as stream 24. Stream 31, depleted in carbon dioxide, is recirculated to the reactor.

The third portion 30 of the overhead stream 12 is treated to remove excess argon. This is achieved by passing stream 30 across the feed side of membrane unit 14.

A synthetic polymer membrane separates the components of a gas or vapor mixture because the components permeate the membrane at different rates. The permeability, P [cm$^3$(STP)•cm/cm$^2$•s•cmHg], of a polymer membrane material for a gas is defined as the rate at which that gas moves through a standard thickness [1 cm] of the material under a standard driving force [a pressure difference of 1 cmHg].

A measure of the ability of a membrane to separate two gases is the selectivity, $\alpha$, defined as the ratio of the gas permeabilities, $P_1/P_2$. The intrinsic selectivity of a polymer material is established by measuring the permeabilities with pure gas or vapor samples, then calculating the ratio. The actual selectivity obtained in a real separation process is established by making permeation measurements with gas mixtures. Selectivity can also be expressed as:

$$\alpha = \frac{D_1}{D_2} \cdot \frac{k_1}{k_2}$$

where D is the diffusion coefficient of the gas in the membrane [cm$^2$/s], which is a measure of the gas mobility, and k is the Henry's law sorption coefficient, which links the concentration of the gas in the membrane material to the pressure in the adjacent gas [cm$^3$(STP)/cm$^2$•cmHg], and is a measure of the gas solubility in the membrane material.

The ratio $D_1/D_2$ is the ratio of the diffusion coefficients of the two gases and can be viewed as the mobility selectivity, reflecting the different sizes of the two molecules. The ratio $k_1/k_2$ is the ratio of the Henry's law coefficients of the two gases and can be viewed as the solubility selectivity, reflecting the relative condensabilities of the two gases.

In all polymer materials, the diffusion coefficient decreases with increasing molecular size. Hence, the diffusion component of the selectivity always favors the passage of small molecules over large ones. The diffusion coefficient thus favors permeation of argon over ethylene. The solubility component of the selectivity, on the other hand, is a measure of the energy required for sorption and normally increases with molecular diameter, because larger molecules are normally more condensable than smaller ones. The solubility coefficient favors permeation of ethylene over argon, therefore. The relative contribution of the diffusion and solubility coefficients determines the overall selectivity of a membrane material.

The balance between diffusion selectivity and solubility selectivity is different for glassy and rubbery polymers. In rubbery polymers, the solubility term is usually the dominant term, so that rubbery membranes are selective for larger, more condensable molecules over smaller, less condensable molecules. Furthermore, since the polymer chains in rubbery membranes are more flexible than in glassy membranes, the fluxes of all permeants, whether the more or less favored permeant, are generally higher through rubbery membranes than through glassy membranes.

In the case of separation of argon from ethylene, both components have fairly small molecules and both have very low boiling points and are not easily condensed. The smaller molecular size of argon means that glassy materials slightly favor the passage of argon over ethylene. The relative condensability of ethylene means that rubbery materials slightly favor the passage of ethylene over argon. However, whether glassy or rubbery membrane materials are used to separate the components, the selectivity is relatively low. For example, polyimides and similar glassy materials have a selectivity for argon over ethylene of up to about 4, and silicone rubber and similar rubbery materials have a similar selectivity of about 4 for ethylene over argon.

It might be supposed, therefore, that it is simply a matter of choice and convenience which type of membrane to use, and that essentially equivalent results will be obtained in either case. This, however, is not so, as we have shown. The difference in performance that can be achieved arises in part from the difference in stage-cuts needed to optimize the membrane separation, depending on whether the residue or the permeate stream is the vented stream. Stage-cut is defined as the ratio of total permeate flow to total feed flow, and is typically expressed as a percentage. For example, a stage-cut of 20% means that of 100 volumes of feed gas, 20 volumes pass to the permeate side and 80 volumes remain on the feed side.

If an argon-selective membrane is used, as is taught in U.S. Pat. Nos. 4,879,396 and 4,904,807, the argon-enriched vent stream is the permeate stream. The composition of this stream, in terms of relative ethylene and argon content, will vary with stage-cut. At low stage-cuts, argon and some ethylene will have permeated the membrane, and the lower the stage-cut, the higher is the argon content and the lower is the ethylene content. Conversely, the higher the stage-cut, the more ethylene will have permeated the membrane and the more ethylene will be lost when the permeate stream is vented. Thus the best results, in terms of capturing ethylene while venting argon, will be obtained at small stage-cuts. However, the stream may often contain two or three times as much ethylene as argon. With the relatively low selectivity available, it is impossible, even at very low stage cut of just a few percent, to avoid venting, at the minimum, about 1 mole of ethylene for every mole of argon vented. In other words, the concentration of ethylene in the purge stream cannot be reduced below a certain theoretical minimum level. Modeling calculations that demonstrate this effect for specific gas compositions are given in the Examples section below.

In contrast, when an ethylene-selective membrane is used, as is taught herein, the argon-enriched purge vent stream is the residue stream. In this case, at low stage-cuts, comparatively little removal of ethylene from the feed stream will have been achieved, and if the residue stream is vented at this point, comparatively large amounts of ethylene will be lost. As the stage-cut increases, a higher proportion of the ethylene passes into the permeate stream, and the higher the stage-cut, the less ethylene will be left in the residue stream. Thus recapture of any amount of ethylene is possible, at least theoretically, by an appropriately high choice of stage-cut. Of course, membrane area required to perform the separation scales in proportion to stage-cut, which will impose a practical limit on recovery, but nevertheless, it is possible to operate with a lower ethylene loss than is possible with an argon-selective membrane, as is again shown by the modeling calculations in the Examples section.

Those of skill in the art will appreciate that the stage-cut used will vary with the specific feed composition, membrane performance and system operating conditions. As a guideline, when dealing with typical ethylene oxide absorber overhead streams, for example containing no more than about 40% ethylene and no more than about 25% argon, it is preferred to operate at a stage-cut of at least about 30%, more preferably at least about 40%, and most preferably at least about 50%. It is expected that stage-cuts of 60%, 70% or even 80% or more may be used in some cases.

Returning to FIG. 1, membrane unit 14 contains ethylene-selective membranes, which generally means rubbery or elastomeric membranes. Examples of polymers that can be used to make elastomeric membranes, include, but are not limited to, nitrile rubber, neoprene, polydimethylsiloxane (silicone rubber), chlorosulfonated polyethylene, polysilicone-carbonate copolymers, fluoroelastomers, plasticized polyvinylchloride, polyurethane, cis-polybutadiene, cis-polyisoprene, poly(butene-1), polystyrene-butadiene copolymers, styrene/butadiene/styrene block copolymers, styrene/ethylene/butylene block copolymers, thermoplastic polyolefin elastomers, and block copolymers of polyethers, polyamides and polyesters. The preferred membrane material is silicone rubber, since silicone rubber membranes are already in commercial production and use for other separations.

As an alternative to a rubbery ethylene-selective membrane, ethylene-selective membranes can also be made from super-glassy materials, such as poly (trimethylsilylpropyne) [PTMSP] and the like, the general use of which is described in U.S. Pat. No. 5,281,255, for example. As yet another alternative, finely microporous inorganic membranes, such as the adsorbent carbon membranes described in U.S. Pat. No. 5,332,424, the pyrolysed carbon membranes described in U.S. Pat. No. 4,685,940, or certain ceramic membranes may be used. These alternatives, most of which exhibit acceptable ethylene selectivity only in the presence of a $C_{3+}$ hydrocarbon or other relatively condensable molecule in the gas mix, and most of which are less readily available than rubbery polymer membranes, are less preferred, but may be useful in some circumstances.

The membrane may take the form of a single homogeneous layer, an integral asymmetric membrane, a multilayer composite membrane, a membrane incorporating a gel or liquid layer or particulates, or any other form known in the art. Composite membranes, in which the elastomeric selective membrane layer is supported on a mechanically strong, highly permeable support layer, are preferred.

The membranes may be manufactured as flat sheets or as fibers and housed in any convenient module form, including spiral-wound modules, plate-and-frame modules and potted hollow-fiber modules. The making of all these types of membranes and modules is well known in the art. Flat-sheet membranes in spiral-wound modules are our most preferred choice.

Membrane unit 14 may contain a single membrane module or bank of modules or an array of modules. A single-stage membrane separation operation is adequate for many applications. If the residue stream requires further purification, it may be passed to a second bank of modules for a second processing step. If the permeate stream requires further concentration, it may be passed to a second bank of modules for a second-stage treatment. Such multistage or multistep processes, and variants thereof, will be familiar to those of skill in the art, who will appreciate that the membrane separation step may be configured in many possible ways, including single-stage, multistage, multistep, or more complicated arrays of two or more units in series or cascade arrangements. If an array of membranes is used, the stage-cut preferences cited above for obtaining good ethylene recovery refer to the overall stage-cut of the array. In other words, the stage-cut is the ratio of total product permeate stream flow to raw feed flow to the first membrane bank in the array. For example, in the two-stage membrane array shown in FIG. 7, described in more detail as it pertains to the Examples, the stage-cut is the ratio of volume flow of stream 708 to streams 701 or 702 expressed as a percentage. Likewise, in the two-step array shown in FIG. 6, the stage-cut is the ratio of volume flow of stream 608 to streams 601 or 602 expressed as a percentage.

A pressure difference between the feed and permeate sides of the membrane is used to provide a driving force for transmembrane permeation. Ethylene oxide reactors are usually run at pressures of a few hundred psi, such as 200 psia or 300 psia, and the gas from the ethylene oxide absorber is recompressed to reactor pressure by compressor 12 for recirculation. Thus, it is normally possible, and is preferred, to operate the membrane system at the feed pressure available from the reactor recompressor without additional compression. If it is desired to increase the pressure difference across the membrane, this can be done by passing the membrane feed stream 30 through an additional compressor or by lowering the pressure on the permeate side by means of a vacuum pump, for example.

The membrane unit separates the feed stream 30 into permeate stream 16 and residue stream 15. The residue stream is vented from the process to any appropriate destination. For a typical stream, unless a very high stage-cut, such as about 80% or above is used, the residue stream will be slightly enriched in methane content compared with the membrane feed stream. Therefore, as in prior art processes, the stream may be incinerated or used as fuel. However, in the process of the invention, this will result in a much smaller loss of ethylene than was previously possible. By following the teachings given herein, it is possible to reduce the ethylene loss per mole of argon vented by as much as 50%, 60%, 70%, 80%, 90%, or even more.

Permeate stream 16, now enriched in ethylene content, could also be passed to any desired destination, although it is preferred to recirculate it to the reactor loop. This stream is recompressed to the loop pressure by compressor 17, and passes as recompressed stream 18 back into the return line 31 of the reaction loop.

It will be apparent to those of skill in the art that the relative sizes of stream 26, 30 and 19 are selected to maintain the desired concentration of carbon dioxide and argon in the reactor gas mix in accordance with plant specifications, and can be adjusted as necessary. As just one example, about half of the absorber overhead stream 12 might be recirculated directly, and the remaining half split about equally between the carbon dioxide purge system and the argon purge system. Typically, however, the argon purge feed 30 will be comparatively small, such as only 1%, 2%, 5% or 10% of stream 12.

An alternative embodiment in which the argon and carbon dioxide purge operations are carried out in series is shown in FIG. 2. Turning to this figure, ethylene, stream 101, and oxygen, stream 102, enter the process and are mixed with recirculating gas, 131. The stream passes through heat exchanger 106 and enters reactor 103 as feed stream 110. The reactor is cooled by passing water in at line 104 and withdrawing steam at line 105. Gas containing the newly formed ethylene oxide exits the reactor as stream 107, is cooled by heat exchange against incoming stream 110, and passes to absorber 108. Water enters the absorber as stream 109; an aqueous solution of ethylene oxide is withdrawn as stream 111 and passes to a purification train, indicated as column 127. Ethylene oxide product is withdrawn as stream 128; water and any remaining contaminants are withdrawn as stream 129.

The overhead stream 112 from the ethylene oxide absorber passes through compressor 113 and is split into two portions in this case. Stream 126 is recirculated to the reactor. Stream 118 is passed to the carbon dioxide purge system scrubbing column 120. Scrubbing solution 125 flows down the scrubber and exits as stream 121. Stream 121 passes through heat exchanger 122 and into regeneration unit 123. Clean scrubbing solution 125 is recirculated and waste carbon dioxide is vented as stream 124. The carbon-dioxide-depleted stream 131 exits the top of column 120. A portion 130, which may any fraction of stream 131, is split from the rest and passes as feed to membrane unit 114, which separates it into residue stream 115 and permeate stream 116. Permeate stream 116, enriched in ethylene and carbon dioxide, is recompressed in compressor 117 and joins the recirculation loop. Stream 115 is purged from the process.

Based on the description of FIGS. 1 and 2, those of skill in the art will appreciate that various other configurations are possible within the scope of the invention. As one example, stream 18 of FIG. 1 can itself be subjected to a carbon dioxide removal treatment before recirculation. As another example, the argon purge membrane system 114 can be positioned in series before the carbon dioxide purge treatment. That is, the apparatus arrangement shown in FIG. 2 can be reversed, so that membrane unit 114 is installed in line 118, or on a bypass line parallel to line 118, upstream of the carbon dioxide removal unit.

Thus, the scope of the invention is not limited to any specific configuration but to the use of an ethylene-selective membrane to provide improved argon-purging capability.

Similarly, although FIGS. 1 and 2 relate primarily to an oxygen-oxidation process, the process of the invention can also be carried out with air-oxidation reactors. In this case, the membrane system can be installed on the main vent from the purge absorber to recover nitrogen from the nitrogen purge stream, for example.

In another aspect, the invention is apparatus useful for ethylene oxide manufacture. In this aspect, the invention includes the following elements:
(a) a reactor for reacting ethylene and oxygen;
(b) an ethylene oxide removal unit connected to the reactor so that gas can pass from the reactor into the ethylene oxide removal unit;
(c) a carbon dioxide removal unit connected to the ethylene oxide removal unit;
(e) a membrane unit containing a membrane selectively permeable to ethylene over argon and connected to the ethylene oxide removal unit;
(f) one or more lines for recirculating gases from the ethylene oxide removal unit, the carbon dioxide removal unit and the membrane unit to the reactor.

As was discussed with regard to the process embodiments, many variations in the specific configuration are possible. For example, with reference to FIG. 1, 3 is the reactor; absorber 8, and the following purification train, form the ethylene oxide removal unit; absorber 20, and the following regeneration train, form the carbon dioxide removal unit; the membrane unit is 14; and the line for recirculating gases is formed by lines 30, 18 and 26 connecting into line 31.

With reference to FIG. 2, 103 is the reactor; absorber 108, and the following purification train, form the ethylene oxide removal unit; absorber 120, and the following regeneration train, form the carbon dioxide removal unit; the membrane unit is 114; and the line for recirculating gases is formed by lines 126, 116 and 131. In this case, the connection of the membrane unit to the ethylene oxide removal unit is indirect, through the carbon dioxide removal unit.

In yet another aspect, the invention is a process for treating an argon purge stream to vent argon and recapture ethylene. In this aspect, the invention comprises:
(a) providing a membrane having a feed side and a permeate side, and being selectively permeable to ethylene over argon;
(b) passing at least a portion of the purge stream across the feed side under conditions in which there is a pressure drop from the feed side to the permeate side;
(c) withdrawing from the feed side an argon-rich stream enriched in argon and depleted in ethylene compared with the purge stream;
(d) withdrawing from the permeate side an ethylene-rich permeate stream enriched in ethylene and depleted in argon compared with the purge stream;
(h) recirculating at least a portion of the ethylene-rich permeate stream to the ethylene oxide manufacturing process;
said process being characterized by a stage-cut between the ethylene-rich permeate stream and the purge stream of at least about 30%.

The invention has been described as it relates to the manufacture of ethylene oxide, and to the production of an argon purge stream with reduced ethylene content. In fact, by modifying the details of the configuration appropriately, a similar process can be carried out in any situation where an oxidation reactor is used in a multiple pass, loop mode, and where avoidance of build-up of an inert gas, particularly argon or nitrogen, in the loop requires continuous or occasional purging. Examples of other materials produced in this way in gasphase reactors, include, but are not limited to:

Acetaldehyde, vinyl acetate and vinyl chloride, produced directly or indirectly from ethylene Propylene oxide and acrylonitrile, produced from propylene Benzoic acid, produced from toluene Caprolactam, produced from cyclohexane Maleic acid, maleic anhydride and phthalic anhydride, produced from various aromatic feedstocks Phenol, produced from cumene Terephthalic acid, produced from p-xylene.

In any of these cases, the process of the invention can be carried out in a manner described in a general way as follows:
(a) reacting an organic reagent and oxygen in a reactor to form an organic product;
(b) withdrawing from the reactor a product stream comprising the organic product, the organic reagent and argon;
(c) removing at least a portion of the organic product from the product stream to form a non-product stream;
(d) providing a membrane having a feed side and a permeate side, and being selectively permeable to the organic reagent over argon;
(e) contacting the feed side with the non-product stream;
(f) withdrawing from the feed side an argon-rich purge stream enriched in argon and depleted in organic reagent compared with the non-product stream;
(g) withdrawing from the permeate side an organic-reagent-rich permeate stream enriched in organic reagent and depleted in argon compared with the non-product stream;

(h) recirculating at least a portion of the organic-reagent-rich permeate stream to the reactor.

Depending on the specific properties of the reagents and products, it may in some cases be desirable to substitute an argon-selective membrane, so that the permeate stream is the purge stream and the residue stream is the reagent-rich stream.

Yet another related process is the oxychlorination of ethylene, in which ethylene, oxygen and hydrogen chloride are reacted in the presence of a fluid catalyst to produce ethylene dichloride. The reaction can be represented as:

$$2C_2H_4 + 4HCl + O_2 \rightarrow 2C_2H_4Cl_2 + 2H_2O$$

The reaction products are sent to a condensation step where the ethylene dichloride and water are removed. A portion of the remaining gas must then be purged and/or treated to remove excess argon, nitrogen, carbon dioxide and carbon monoxide before recirculation to the reactor. A typical purge stream has the following composition:

Ethylene 20–40%
Nitrogen 40–60%
Argon 5–10%
$CO/CO_2$ 2–5%
Oxygen 2–5%
Ethylene dichloride 2–5%
Ethylene chloride 1–2%.

It will be apparent to those of skill in the art that the processes taught herein are also applicable to treat purge streams from reactors of this type to recover ethylene, ethylene chloride and ethylene dichloride, while removing excess inerts.

The invention is now illustrated in further detail by specific examples. These examples are intended to further clarify the invention, and are not intended to limit the scope in any way.

EXAMPLES

Example 1
Permeation Properties of Silicone Rubber Membrane Stamps

A microporous support membrane was dip-coated in a 6% dimethyl siloxane solution at 1 ft/min coating speed, then dried in an oven at 60° C. to crosslink the membrane. The resulting membranes had a nominal selective layer thickness of 2.7 μm. Samples of the finished composite membrane were cut into 12.6 cm² stamps and tested in a permeation test-cell apparatus with pure oxygen, nitrogen, argon, methane, ethylene, and carbon dioxide at 23° C. feed temperature, 50 psig feed pressure, and ambient permeate pressure. The gas fluxes of the membranes were measured, and the selectivities were calculated. The results of the tests are shown in Table 1. Any membrane with a selectivity less than the intrinsic selectivity of the material was considered defective.

TABLE 1

| Gas | Flux × $10^{-6}$ cm³(STP)/cm² · sec · cmHg | Gas/Nitrogen Selectivity (–) |
|---|---|---|
| Nitrogen | 105 | — |
| Oxygen | 228 | 2.2 |
| Argon | 236 | 2.2 |

TABLE 1-continued

| Gas | Flux × $10^{-6}$ cm³(STP)/cm² · sec · cmHg | Gas/Nitrogen Selectivity (–) |
|---|---|---|
| Methane | 348 | 3.3 |
| Ethylene | 983 | 9.4 |
| Carbon Dioxide | 1,360 | 13.0 |

Examples 2–6
Ethylene/Argon Separation Using an Argon-Selective Membrane

Example 2

Figure 3:
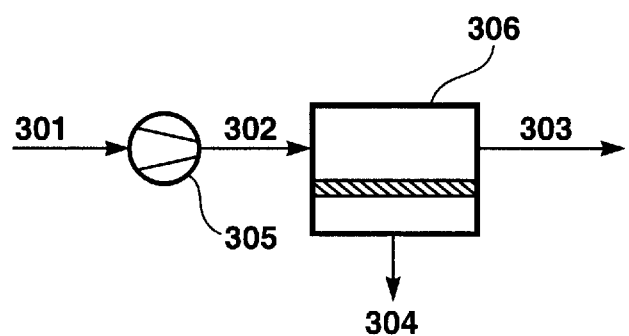
FIG. 3 is a schematic drawing of a one-stage membrane separation unit and process.

A series of computer calculations were performed with a modeling program, ChemCad III (ChemStations, Inc., Houston, Tex.), to illustrate the effect of stage-cut on an ethylene/argon separation process using an argon-selective membrane. For simplicity, the feed stream was assumed to have only three components: 30% ethylene, 10% argon, and 60% methane, approximating the composition of gas from the reactor after carbon dioxide and ethylene oxide removal. Membrane pressure-normalized fluxes were assumed to be as follows, as are typical of glassy membranes:

Ethylene $5 \times 10^{-6}$ cm³(STP)/cm²·sec·cmHg
Argon $20 \times 10^{-6}$ cm³(STP)/cm²·sec·cmHg
Methane $5 \times 10^{-6}$ cm³(STP)/cm²·sec·cmHg We assumed a one-stage separation as in FIG. 3. In this Figure, line 301 carries the overhead stream from the ethylene oxide absorber through compressor 305. The compressed stream in line 302 enters the membrane unit, 306, where most of the argon and some of the ethylene and methane permeate the membrane and are withdrawn through line 304. The residue stream, withdrawn through line 303, is depleted of argon and enriched in ethylene and methane. The stage-cut was assumed to be 63%. The results of the calculations are shown in Table 2.

TABLE 2

| Component/Parameter | Stream 301 | Stream 302 | Stream 303 | Stream 304 |
|---|---|---|---|---|
| Mass Flow Rate (lb/h) | 368.3 | 368.3 | 126.3 | 242.0 |
| Flow Rate (scfm) | 100 | 100 | 37.1 | 62.9 |
| Temperature (°C.) | 25 | 227 | 226 | 226 |
| Pressure (psia) | 15 | 200 | 200 | 20 |
| Component (mol %) | | | | |
| Ethylene | 30.0 | 30.0 | 32.8 | 28.3 |
| Argon | 10.0 | 10.0 | 1.5 | 15.0 |
| Methane | 60.0 | 60.0 | 65.6 | 56.7 |

Membrane Area: 566 m²

Example 3

A computer calculation was performed as in Example 2, except the stage-cut was assumed to be 34%. The results of the calculations are shown in Table 3.

TABLE 3

| Component/Parameter | Stream 301 | Stream 302 | Stream 303 | Stream 304 |
|---|---|---|---|---|
| Mass Flow Rate (lb/h) | 368.3 | 368.3 | 230.5 | 137.8 |
| Flow Rate (scfm) | 100 | 100 | 65.7 | 34.3 |

TABLE 3-continued

| Component/Parameter | Stream 301 | Stream 302 | Stream 303 | Stream 304 |
|---|---|---|---|---|
| Temperature (°C.) | 25 | 227 | 226 | 226 |
| Pressure (psia) | 15 | 200 | 200 | 20 |
| Component (mol %) | | | | |
| Ethylene | 30.0 | 30.0 | 31.7 | 26.7 |
| Argon | 10.0 | 10.0 | 4.8 | 20.0 |
| Methane | 60.0 | 60.0 | 63.5 | 53.3 |

Membrane Area: 296 m$^2$

Example 4

A computer calculation was performed as in Example 2, except the stage-cut was assumed to be 7%. The results of the calculations are shown in Table 4.

TABLE 4

| Component/Parameter | Stream 301 | Stream 302 | Stream 303 | Stream 304 |
|---|---|---|---|---|
| Mass Flow Rate (lb/h) | 368.3 | 368.3 | 338.6 | 29.7 |
| Flow Rate (scfm) | 100 | 100 | 92.9 | 7.1 |
| Temperature (°C.) | 25 | 227 | 227 | 227 |
| Pressure (psia) | 15 | 200 | 200 | 20 |
| Component (mol %) | | | | |
| Ethlene | 30.0 | 30.0 | 30.4 | 25.0 |
| Argon | 10.0 | 10.0 | 8.8 | 25.0 |
| Methane | 60.0 | 60.0 | 60.8 | 50.0 |

Membrane Area: 59 m$^2$

Example 5

A computer calculation was performed as in Example 2, except the stage-cut was assumed to be 0.6%. The results of the calculations are shown in Table 5.

TABLE 5

| Component/Parameter | Stream 301 | Stream 302 | Stream 303 | Stream 304 |
|---|---|---|---|---|
| Mass Flow Rate (lb/h) | 368.3 | 368.3 | 365.7 | 2.6 |
| Flow Rate (scfm) | 100 | 100 | 99.4 | 0.6 |
| Temperature (°C.) | 25 | 227 | 227 | 227 |
| Pressure (psia) | 15 | 200 | 200 | 20 |
| Component (mol %) | | | | |
| Ethylene | 30.0 | 30.0 | 30.0 | 24.6 |
| Argon | 10.0 | 10.0 | 9.9 | 26.2 |
| Methane | 60.0 | 60.0 | 60.1 | 49.2 |

Membrane Area: 5 m$^2$

Figure 4:
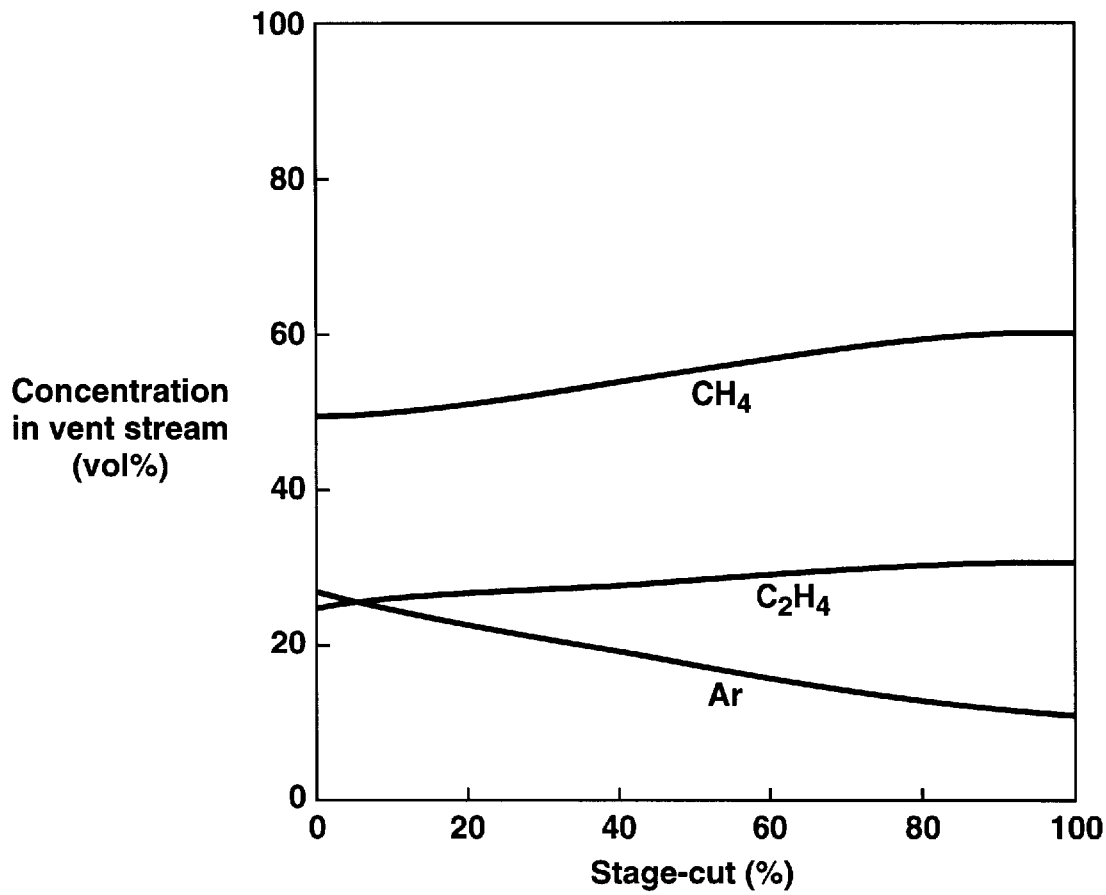
FIG. 4 is a graph showing the relationship between membrane stage-cut and component concentration in the vent stream from the membrane for an argon-selective membrane.

Example 6
Comparison of Vent Stream Concentrations as a Function of Stage-Cut FIG. 4 is a graph showing the concentrations of methane, ethylene and argon in the vent stream as a function of stage-cut, according to the calculations in Examples 2–5. As can be seen, the lower stage-cuts yielded the highest argon concentration and the lowest ethylene concentration in the vent (permeate) stream. Thus, to obtain the highest ethylene recovery in the product (residue) stream, it is desirable to operate the process at the lowest stage-cut possible. Even at the lowest stage-cuts, however, the concentration of ethylene in the vent stream is only reduced from 30% to about 25%.

Examples 7–14
Ethylene/Argon Separation According to the Process of the Invention

Example 7

A series of computer calculations were performed with the ChemCad III modeling program to illustrate the effect of various stage-cuts on an ethylene/argon separation process according to the process of the invention using an ethylene-selective membrane. For simplicity, the feed stream was assumed to have only three components: 30% ethylene, 10% argon, and 60% methane. We assumed membrane pressure-normalized fluxes as follows, as are typical of rubbery membranes:

Ethylene $100\times10^{-6}$ cm$^3$(STP)/cm$^2 \cdot$sec$\cdot$cmHg

Argon $25\times10^{-6}$ cm$^3$(STP)/cm$^2 \cdot$sec$\cdot$cmHg

Methane $35\times10^{-6}$ cm$^3$(STP)/cm$^2 \cdot$sec$\cdot$cmHg

We assumed a one-stage separation as in FIG. 3. In this example, however, the permeate stream withdrawn through line 304 contains mostly ethylene and methane. Most of the argon, along with some ethylene and methane, is withdrawn as a residue stream through line 303. The stage-cut was assumed to be 37%. The results of the calculations are shown in Table 6.

TABLE 6

| Component/Parameter | Stream 301 | Stream 302 | Stream 303 | Stream 304 |
|---|---|---|---|---|
| Mass Flow Rate (lb/h) | 368.3 | 368.3 | 224.7 | 143.5 |
| Flow Rate (scfm) | 100 | 100 | 62.8 | 37.2 |
| Temperature (°C.) | 25 | 227 | 226 | 226 |
| Pressure (psia) | 15 | 200 | 200 | 20 |
| Component (mol %) | | | | |
| Ethylene | 30.0 | 30.0 | 20.0 | 46.9 |
| Argon | 10.0 | 10.0 | 12.4 | 6.0 |
| Methane | 60.0 | 60.0 | 67.6 | 47.1 |

Membrane Area: 39 m$^2$

Example 8

A computer calculation was performed as in Example 7, except the stage-cut was assumed to be 66%. The results of the calculations are shown in Table 7.

TABLE 7

| Component/Parameter | Stream 301 | Stream 302 | Stream 303 | Stream 304 |
|---|---|---|---|---|
| Mass Flow Rate (lb/h) | 368.3 | 368.3 | 118.5 | 249.8 |
| Flow Rate (scfm) | 100 | 100 | 33.8 | 66.2 |
| Temperature (°C.) | 25 | 227 | 225 | 225 |
| Pressure (psia) | 15 | 200 | 200 | 20 |
| Component (mol %) | | | | |
| Ethylene | 30.0 | 30.0 | 10.0 | 40.2 |
| Argon | 10.0 | 10.0 | 15.7 | 7.1 |
| Methane | 60.0 | 60.0 | 74.3 | 52.7 |

Membrane Area: 74 m$^2$

Example 9

A computer calculation was performed as in Example 7, except the stage-cut was assumed to be 80%. The results of the calculations are shown in Table 8.

TABLE 8

| Component/Parameter | Stream 301 | Stream 302 | Stream 303 | Stream 304 |
|---|---|---|---|---|
| Mass Flow Rate (lb/h) | 368.3 | 368.3 | 70.5 | 297.8 |
| Flow Rate (scfm) | 100 | 100 | 20.0 | 80.0 |
| Temperature (°C.) | 25 | 227 | 225 | 225 |
| Pressure (psia) | 15 | 200 | 200 | 20 |
| Component (mol %) | | | | |
| Ethylene | 30.0 | 30.0 | 5.0 | 36.3 |
| Argon | 10.0 | 10.0 | 18.4 | 7.9 |
| Methane | 60.0 | 60.0 | 76.6 | 55.8 |

Membrane Area: 92 m$^2$

Example 10

A computer calculation was performed as in Example 7, except the stage-cut was assumed to be 86%. The results of the calculations are shown in Table 9.

TABLE 9

| Component/Parameter | Stream 301 | Stream 302 | Stream 303 | Stream 304 |
|---|---|---|---|---|
| Mass Flow Rate (lb/h) | 368.3 | 368.3 | 49.8 | 318.4 |
| Flow Rate (scfm) | 100 | 100 | 14.0 | 86.0 |
| Temperature (°C.) | 25 | 227 | 225 | 225 |
| Pressure (psia) | 15 | 200 | 200 | 20 |
| Component (mol %) | | | | |
| Ethylene | 30.0 | 30.0 | 3.0 | 34.4 |
| Argon | 10.0 | 10.0 | 20.3 | 8.3 |
| Methane | 60.0 | 60.0 | 76.7 | 57.3 |

Membrane Area: 101 m$^2$

Example 11

A computer calculation was performed as in Example 7, except the stage-cut was assumed to be 89%. The results of the calculations are shown in Table 10.

TABLE 10

| Component/Parameter | Stream 301 | Stream 302 | Stream 303 | Stream 304 |
|---|---|---|---|---|
| Mass Flow Rate (lb/h) | 368.3 | 368.3 | 38.4 | 329.9 |
| Flow Rate (scfm) | 100 | 100 | 10.7 | 89.3 |
| Temperature (°C.) | 25 | 227 | 225 | 225 |
| Pressure (psia) | 15 | 200 | 200 | 20 |
| Component (mol %) | | | | |
| Ethylene | 30.0 | 30.0 | 2.0 | 33.3 |
| Argon | 10.0 | 10.0 | 21.7 | 8.6 |
| Methane | 60.0 | 60.0 | 76.3 | 58.1 |

Membrane Area: 106 m$^2$

Example 12

A computer calculation was performed as in Example 7, except the stage-cut was assumed to be 93%. The results of the calculations are shown in Table 11.

TABLE 11

| Component/Parameter | Stream 301 | Stream 302 | Stream 303 | Stream 304 |
|---|---|---|---|---|
| Mass Flow Rate (lb/h) | 368.3 | 368.3 | 24.9 | 343.4 |
| Flow Rate (scfm) | 100 | 100 | 6.8 | 93.2 |
| Temperature (°C.) | 25 | 227 | 225 | 225 |
| Pressure (psia) | 15 | 200 | 200 | 20 |
| Component (mol %) | | | | |
| Ethylene | 30.0 | 30.0 | 1.0 | 32.1 |
| Argon | 10.0 | 10.0 | 24.2 | 9.0 |
| Methane | 60.0 | 60.0 | 74.8 | 58.9 |

Membrane Area: 112 m$^2$

Example 13

A computer calculation was performed as in Example 7, except the stage-cut was assumed to be 96%. The results of the calculations are shown in Table 12.

TABLE 12

| Component/Parameter | Stream 301 | Stream 302 | Stream 303 | Stream 304 |
|---|---|---|---|---|
| Mass Flow Rate (lb/h) | 368.3 | 368.3 | 16.4 | 351.9 |
| Flow Rate (scfm) | 100 | 100 | 4.4 | 95.6 |
| Temperature (°C.) | 25 | 227 | 225 | 225 |
| Pressure (psia) | 15 | 200 | 200 | 20 |
| Component (mol %) | | | | |
| Ethylene | 30.0 | 30.0 | 0.5 | 31.3 |
| Argon | 10.0 | 10.0 | 26.6 | 9.2 |
| Methane | 60.0 | 60.0 | 72.9 | 59.4 |

Membrane Area: 115 m$^2$

Example 14

Comparison of Vent Stream Concentrations as a Function of Stage-Cut

Figure 5:
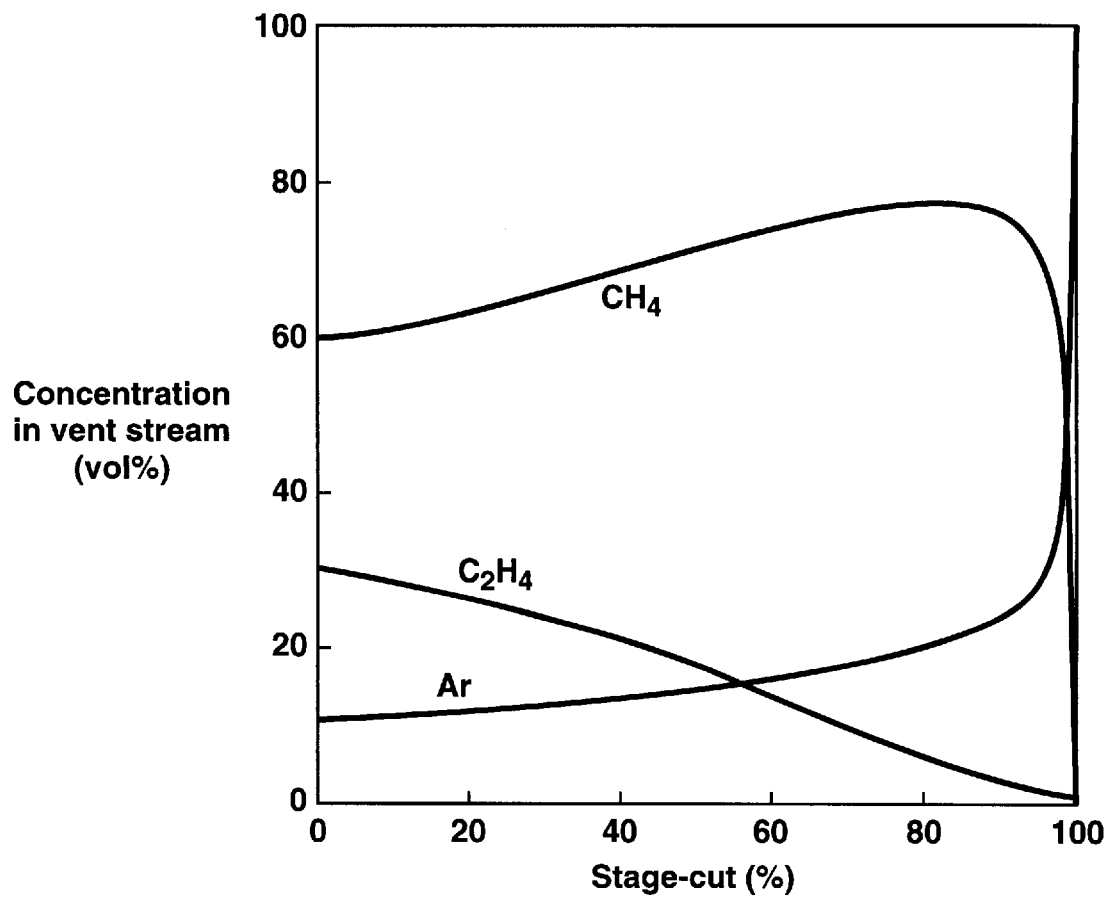
FIG. 5 is a graph showing the relationship between membrane stage-cut and component concentration in the vent stream from the membrane for an ethylene-selective membrane.

FIG. 5 is a graph showing the concentrations of methane, ethylene and argon in the vent stream as a function of stage-cut, according to the calculations in Examples 7–13. As can be seen, the higher stage-cuts yielded the highest argon concentration and the lowest ethylene concentration in the vent (residue) stream. Thus, to obtain the highest ethylene recovery in the product (permeate) stream, it is desirable to operate the process at the highest stage-cut possible. At stage-cuts above about 85%, ethylene losses can be almost eliminated. Thus, there is no inherent limit on ethylene recovery, as is the case with the argon-selective membrane calculations of Examples 2–5.

Example 15

FIG. 5 was used to interpolate the ethylene loss and ethylene recovery that can be obtained at various stage-cuts with the process of the invention. The results of the calculations are shown in Table 13. The ethylene loss was expressed as the ratio of moles of ethylene in the vent (residue) stream to moles of argon in the vent stream. The methylene loss was likewise expressed as the ratio of moles of methane in the vent stream to moles of argon in the vent stream. The ethylene recovery was defined as the difference in ethylene loss with and without the membrane recovery process, expressed as a percentage of the ethylene loss without the membrane recovery process. For example, since the feed composition is 30% ethylene, 10% argon, and 60% methane, if no membrane recovery step is in place, the purging operation would release 3 moles of ethylene for every 1 mole of argon released. In the 60% stage-cut case, 13/15 (0.87) moles of ethylene are released for every mole of argon released. Thus the ethylene recovery provided by the membrane step is (3−0.87)=2.13 moles, or 2.13/3=71% recovery compared with the "no-membrane" case.

TABLE 13

| Stage-Cut (%) | Concentration in Vent Stream (mol %) | | | Ethylene Loss (moles/mole argon) | Methane Loss (moles/mole argon) | Ethylene Recovery (%) |
| --- | --- | --- | --- | --- | --- | --- |
| | Argon | Ethylene | Methane | | | |
| 90 | 23 | 2 | 76 | 0.09 | 3.3 | 97 |
| 80 | 19 | 5 | 77 | 0.26 | 4.1 | 91 |
| 70 | 16 | 9 | 75 | 0.56 | 4.7 | 81 |
| 60 | 15 | 13 | 73 | 0.87 | 4.9 | 71 |

Examples 16–19

Argon-Selective-Membrane Process on a Multi-Component Stream

Example 16

Calculations were performed as in Example 2, to determine the separation that can be achieved by a one-stage membrane process as in FIG. 3. This time, the feed mixture was chosen to be more closely representative of an actual vent stream from an ethylene oxide reactor, and was assumed to contain the following components in the concentrations noted:

28% Ethylene

6% Oxygen 3.5% Carbon Dioxide

2% Nitrogen

10% Argon 50.5% Methane

Membrane pressure-normalized fluxes were assumed to be as follows, which are typical of polyimide membranes:

Ethylene $5\times10^{-6}$ cm$^3$(STP)/cm$^2 \cdot$sec$\cdot$cmHg

Oxygen $25\times10^{-6}$ cm$^3$(STP)/cm$^2 \cdot$sec$\cdot$cmHg

Carbon Dioxide $200\times10^{-6}$ cm$^3$(STP)/cm$^2 \cdot$sec$\cdot$cmHg

Nitrogen $5\times10^{-6}$ cm$^3$(STP)/cm$^2 \cdot$sec$\cdot$cmHg

Argon $20\times10^{-6}$ cm$^3$(STP)/cm$^2 \cdot$sec$\cdot$cmHg

Methane $5\times10^{-6}$ cm$^3$(STP)/cm$^2 \cdot$sec$\cdot$cmHg

The stage-cut was set at 5.4%. The results of the calculation are shown in Table 14.

TABLE 14

| Component/Parameter | Stream 301 | Stream 302 | Stream 303 | Stream 304 |
| --- | --- | --- | --- | --- |
| Mass Flow Rate (lb/h) | 400.6 | 400.6 | 372.8 | 27.8 |
| Flow Rate (scfm) | 100 | 100 | 94.6 | 5.4 |
| Temperature (°C.) | 25 | 207 | 207 | 207 |
| Pressure (psia) | 20 | 200 | 200 | 20 |
| Component (mol %) | | | | |
| Ethylene | 28.0 | 28.0 | 28.7 | 16.2 |
| Oxygen | 6.0 | 6.0 | 5.6 | 13.4 |
| Carbon Dioxide | 3.5 | 3.5 | 2.5 | 21.1 |
| Nitrogen | 2.0 | 2.0 | 2.0 | 1.1 |
| Argon | 10.0 | 10.0 | 9.5 | 19.0 |
| Methane | 50.5 | 50.5 | 51.7 | 29.2 |

Membrane Area: 30 m$^2$

Table 15 shows the ethylene loss that occurs when the parameters in Table 14 are used. Also shown is the improvement in ethylene recovery compared to a reactor that does not use a membrane process to treat the vent stream. A normalizing factor was applied to the membrane area, so that in all cases the removal/recovery calculations could be compared on the basis of a vent stream that will release 10 scfm of argon.

TABLE 15

| Component | Ethylene | Oxygen | Carbon Dioxide | Nitrogen | Argon | Methane |
| --- | --- | --- | --- | --- | --- | --- |
| Concentration in vent stream (mol %) | 16.2 | 13.4 | 21.1 | 1.1 | 19.0 | 29.2 |
| Moles lost/mole of argon vented | 0.85 | 0.71 | 1.11 | 0.06 | 1.0 | 1.54 |
| Moles lost/mole of argon vented (No membrane) | 2.8 | 0.6 | 0.35 | 0.2 | 1.0 | 5.05 |
| Removal/Recovery compared to No membrane (%) | 69.6 | (18.3) | (217) | 70 | — | 69.5 |

Membrane Area: 291 m$^2$

Example 17

The calculations of Example 16 were repeated, except at a stage-cut of 8.8%. The results of the calculations are shown in Table 16.

TABLE 16

| Component/Parameter | Stream 301 | Stream 302 | Stream 303 | Stream 304 |
|---|---|---|---|---|
| Mass Flow Rate (lb/h) | 400.6 | 400.6 | 356.2 | 44.4 |
| Flow Rate (scfm) | 100 | 100 | 91.2 | 8.8 |
| Temperature (°C.) | 25 | 207 | 207 | 207 |
| Pressure (psia) | 20 | 200 | 200 | 20 |
| Component (mol %) | | | | |
| Ethylene | 28.0 | 28.0 | 29.1 | 16.8 |
| Oxygen | 6.0 | 6.0 | 5.3 | 13.4 |
| Carbon Dioxide | 3.5 | 3.5 | 2.0 | 19.2 |
| Nitrogen | 2.0 | 2.0 | 2.1 | 1.2 |
| Argon | 10.0 | 10.0 | 9.1 | 19.1 |
| Methane | 50.5 | 50.5 | 52.4 | 30.3 |

Membrane Area: 50 m$^2$

Table 17 shows the ethylene loss that occurs when the parameters in Table 16 are used. Also shown is the improvement in ethylene recovery compared to a reactor that does not use a membrane process to treat the vent stream. A normalizing factor was applied to the membrane area, so that in all cases the removal/recovery calculations could be compared on the basis of a vent stream that will release 10 scfm of argon.

TABLE 17

| Component | Ethylene | Oxygen | Carbon Dioxide | Nitrogen | Argon | Methane |
|---|---|---|---|---|---|---|
| Concentration in vent stream (mol %) | 16.8 | 13.4 | 19.2 | 1.2 | 19.1 | 30.3 |
| Moles lost/mole of argon vented | 0.88 | 0.70 | 1.0 | 0.63 | 1.0 | 1.59 |
| Moles lost/mole of argon vented (No membrane) | 2.8 | 0.6 | 0.35 | 0.2 | 1.0 | 5.05 |
| Removal/Recovery compared to No membrane (%) | 68.6 | (16.7) | (186) | (215) | — | 68.5 |

Membrane Area: 298 m$^2$

Example 18

The calculations of Example 16 were repeated, except at a stage-cut of 16.5%. The results of the calculations are shown in Table 18.

TABLE 18

| Component/Parameter | Stream 301 | Stream 302 | Stream 303 | Stream 304 |
|---|---|---|---|---|
| Mass Flow Rate (lb/h) | 400.6 | 400.6 | 319.7 | 80.9 |
| Flow Rate (scfm) | 100 | 100 | 83.5 | 16.5 |
| Temperature (°C.) | 25 | 207 | 207 | 207 |
| Pressure (psia) | 20 | 200 | 200 | 20 |
| Component (mol %) | | | | |
| Ethylene | 28.0 | 28.0 | 29.9 | 18.1 |
| Oxygen | 6.0 | 6.0 | 4.6 | 13.2 |
| Carbon Dioxide | 3.5 | 3.5 | 1.1 | 15.5 |
| Nitrogen | 2.0 | 2.0 | 2.1 | 1.3 |
| Argon | 10.0 | 10.0 | 8.2 | 19.2 |
| Methane | 50.5 | 50.5 | 54.0 | 32.7 |

Membrane Area: 100 m$^2$

Table 19 shows the ethylene loss that occurs when the parameters in Table 18 are used. Also shown is the improvement in ethylene recovery compared to a reactor that does not use a membrane process to treat the vent stream. A normalizing factor was applied to the membrane area, so that in all cases the removal/recovery calculations could be compared on the basis of a vent stream that will release 10 scfm of argon.

TABLE 19

| Component | Ethylene | Oxygen | Carbon Dioxide | Nitrogen | Argon | Methane |
|---|---|---|---|---|---|---|
| Concentration in vent stream (mol %) | 18.1 | 13.2 | 15.5 | 1.3 | 19.2 | 32.7 |
| Moles lost/mole of argon vented | 0.94 | 0.69 | 0.81 | 0.07 | 1.0 | 1.7 |
| Moles lost/mole of argon vented (No membrane) | 2.8 | 0.6 | 0.35 | 0.2 | 1.0 | 5.05 |
| Removal/Recovery compared to No membrane (%) | 66.4 | (15) | (131) | 65 | 0 | 66.3 |

Membrane Area: 317 m$^2$

Example 19

Table 20, compiled from Tables 15, 17, and 19, compares the ethylene losses and the ethylene recovery rates of the argon-selective membrane processes at varying stage-cuts. As can be seen, the lower the stage-cut, the lower is the ethylene loss in the argon vent stream, and the greater is the ethylene recovery. This result is in accordance with FIG. 4 and the calculations of Examples 2–5, which used a three-component feed mixture.

TABLE 20

| Parameter | No membrane | Table 15 | Table 17 | Table 19 |
|---|---|---|---|---|
| Stage-Cut (%) | — | 5.4 | 8.8 | 16.5 |
| Ethylene concentration in vent stream (mol %) | 28.0 | 16.2 | 16.8 | 18.1 |
| Moles of ethylene lost/mole of argon vented | 2.8 | 0.85 | 0.88 | 0.94 |
| Removal/Recovery compared to No membrane (%) | — | 69.6 | 68.6 | 66.4 |

Examples 20–23
Ethylene-Permeable-Membrane Process on a Multi-Component Stream

Example 20

Calculations were performed as in Example 7, to determine the separation that can be achieved by a one-stage membrane process as in FIG. 3. The feed mixture was chosen to be more closely representative of an actual vent stream from an ethylene oxide reactor, and was assumed to contain the following components in the concentrations noted:

28% Ethylene
6% Oxygen
3.5% Carbon Dioxide
2% Nitrogen
10% Argon
50.5% Methane

We assumed membrane pressure-normalized fluxes as follows, which were determined in Example 1 for silicone rubber membranes:

Ethylene $983 \times 10^{-6}$ cm$^3$(STP)/cm$^2$•sec•cmHg
Oxygen $228 \times 10^{-6}$ cm$^3$(STP)/cm$^2$•sec•cmHg
Carbon Dioxide $1,360 \times 10^{-6}$ cm$^3$(STP)/cm$^2$•sec•cmHg
Nitrogen $105 \times 10^{-6}$ cm$^3$(STP)/cm$^2$•sec•cmHg
Argon $236 \times 10^{-6}$ cm$^3$(STP)/cm$^2$•sec•cmHg
Methane $348 \times 10^{-6}$ cm$^3$(STP)/cm$^2$•sec•cmHg The stage-cut was set at 80.3%. The results of the calculation are shown in Table 21.

TABLE 21

| Component/Parameter | Stream 301 | Stream 302 | Stream 303 | Stream 304 |
|---|---|---|---|---|
| Mass Flow Rate (lb/h) | 400.6 | 400.6 | 77.5 | 323.1 |
| Flow Rate (scfm) | 100 | 100 | 19.7 | 80.3 |
| Temperature (°C.) | 25 | 207 | 205 | 205 |
| Pressure (psia) | 20 | 200 | 200 | 20 |
| Component (mol %) | | | | |
| Ethylene | 28.0 | 28.0 | 4.0 | 33.9 |
| Oxygen | 6.0 | 6.0 | 11.4 | 4.7 |
| Carbon Dioxide | 3.5 | 3.5 | 0.2 | 4.3 |
| Nitrogen | 2.0 | 2.0 | 6.4 | 0.9 |
| Argon | 10.0 | 10.0 | 18.4 | 7.9 |
| Methane | 50.5 | 50.5 | 59.7 | 48.2 |

Membrane Area: 10 m$^2$

Table 22 shows the ethylene loss that occurs when the parameters in Table 21 are used. Also shown is the improvement in ethylene recovery compared to a reactor that does not use a membrane process to treat the vent stream. A normalizing factor was applied to the membrane area, so that in all cases the removal/recovery calculations could be compared on the basis of a vent stream that will release 10 scfm of argon.

TABLE 22

| Component | Ethylene | Oxygen | Carbon Dioxide | Nitrogen | Argon | Methane |
|---|---|---|---|---|---|---|
| Concentration in vent stream (mol %) | 4.0 | 11.4 | 0.2 | 6.4 | 18.4 | 59.7 |
| Moles lost/mole of argon vented | 0.22 | 0.62 | 0.01 | 0.35 | 1.0 | 3.24 |
| Moles lost/mole of argon vented (No membrane) | 2.8 | 0.6 | 0.35 | 0.2 | 1.0 | 5.05 |
| Removal/Recovery compared to No membrane (%) | 92.1 | (3.3) | 97.1 | (75) | — | 35.8 |

Membrane Area: 26.9 m$^2$
Theoretical Horsepower: 38.7

Example 21

Calculations were performed as in Example 20, except with a stage-cut of 87%. The results of the calculations are shown in Table 23.

TABLE 23

| Component/Parameter | Stream 301 | Stream 302 | Stream 303 | Stream 304 |
|---|---|---|---|---|
| Mass Flow Rate (lb/h) | 400.6 | 400.6 | 52.2 | 348.4 |
| Flow Rate (scfm) | 100 | 100 | 13.0 | 87.0 |
| Temperature (°C.) | 25 | 233 | 231 | 231 |
| Pressure (psia) | 15 | 200 | 200 | 20 |
| Component (mol %) | | | | |
| Ethylene | 28.0 | 28.0 | 2.0 | 31.9 |
| Oxygen | 6.0 | 6.0 | 12.6 | 5.0 |

TABLE 23-continued

| Component/Parameter | Stream 301 | Stream 302 | Stream 303 | Stream 304 |
|---|---|---|---|---|
| Carbon Dioxide | 3.5 | 3.5 | 0.07 | 4.0 |
| Nitrogen | 2.0 | 2.0 | 8.3 | 1.1 |
| Argon | 10.0 | 10.0 | 20.1 | 8.5 |
| Methane | 50.5 | 50.5 | 56.9 | 49.5 |

Membrane Area: 11 m$^2$

Table 24 shows the ethylene loss that occurs when the parameters in Table 23 are used. Also shown is the improvement in ethylene recovery compared to a reactor that does not use a membrane process to treat the vent stream. A normalizing factor was applied to the membrane area, so that in all cases the removal/recovery calculations could be compared on the basis of a vent stream that will release 10 scfm of argon.

TABLE 24

| Component | Ethylene | Oxygen | Carbon Dioxide | Nitrogen | Argon | Methane |
|---|---|---|---|---|---|---|
| Concentration in vent stream (mol %) | 2.0 | 12.6 | 0.07 | 8.3 | 20.1 | 56.9 |
| Moles lost/mole of argon vented | 0.10 | 0.63 | 0.003 | 0.41 | 1.0 | 2.83 |
| Moles lost/mole of argon vented (No membrane) | 2.8 | 0.6 | 0.35 | 0.2 | 1.0 | 5.05 |
| Removal/Recovery compared to No membrane (%) | 96.4 | (5) | 99 | (105) | — | 44.0 |

Membrane Area: 41.7 m$^2$
Theoretical Horsepower: 69.5

Example 22

Calculations were performed as in Example 20, except with a stage-cut of 91.2%. The results of the calculation are shown in Table 25.

TABLE 25

| Component/Parameter | Stream 301 | Stream 302 | Stream 303 | Stream 304 |
|---|---|---|---|---|
| Mass Flow Rate (lb/h) | 400.6 | 400.6 | 36.2 | 364.4 |
| Flow Rate (scfm) | 100 | 100 | 8.8 | 91.2 |
| Temperature (°C.) | 25 | 233 | 231 | 231 |
| Pressure (psia) | 15 | 200 | 200 | 20 |
| Component (mol %) | | | | |
| Ethylene | 28.0 | 28.0 | 1.0 | 30.6 |
| Oxygen | 6.0 | 6.0 | 13.6 | 5.3 |
| Carbon Dioxide | 3.5 | 3.5 | 0.03 | 3.8 |
| Nitrogen | 2.0 | 2.0 | 10.6 | |

TABLE 25-continued

| Component/Parameter | Stream 301 | Stream 302 | Stream 303 | Stream 304 |
|---|---|---|---|---|
| Argon | 10.0 | 10.0 | 21.6 | 8.9 |
| Methane | 50.5 | 50.5 | 53.2 | 50.2 |

Membrane Area: 12 m$^2$

Table 26 shows the ethylene loss that occurs when the parameters in Table 25 are used. Also shown is the improvement in ethylene recovery compared to a reactor that does not use a membrane process to treat the vent stream. A normalizing factor was applied to the membrane area, so that in all cases the removal/recovery calculations could be compared on the basis of a vent stream that will release 10 scfm of argon.

TABLE 26

| Component | Ethylene | Oxygen | Carbon Dioxide | Nitrogen | Argon | Methane |
|---|---|---|---|---|---|---|
| Concentration in vent stream (mol %) | 1.0 | 13.6 | 0.03 | 10.6 | 21.6 | 53.2 |
| Moles lost/mole of argon vented | 0.05 | 0.63 | 0.001 | 0.49 | 1.0 | 2.46 |
| Moles lost/mole of argon vented (No membrane) | 2.8 | 0.6 | 0.35 | 0.2 | 1.0 | 5.05 |
| Removal/Recovery compared to No membrane (%) | 98.2 | (5) | 99.7 | (145) | — | 51.3 |

Membrane Area: 61.4 m$^2$
Theoretical Horsepower: 100.3

Example 23

Table 27, compiled from Tables 22, 24, and 26, compares the ethylene losses and the ethylene recovery rates of the process of the invention at varying stage-cuts. As can be seen, the higher the stage-cut, the lower is the ethylene loss in the argon vent stream, and the greater is the ethylene recovery. This result is in accordance with FIG. 5 and the calculations of Examples 7–13, which used a three-component feed mixture.

TABLE 27

| Parameter | No membrane | Table 22 | Table 24 | Table 26 |
|---|---|---|---|---|
| Stage-Cut (%) | — | 80.3 | 87.0 | 91.2 |
| Ethylene concentration in vent stream (mol %) | 28.0 | 4.0 | 2.0 | 1.0 |
| Moles of ethylene lost/mole of argon vented | 2.8 | 0.22 | 0.10 | 0.05 |
| Removal/Recovery compared to No membrane (%) | — | 92.0 | 96.4 | 98.2 |

Examples 24–25
Ethylene-Permeable Multi-step and Multi-stage Membrane Processes on Multi-Component Streams

Example 24

Figure 6:
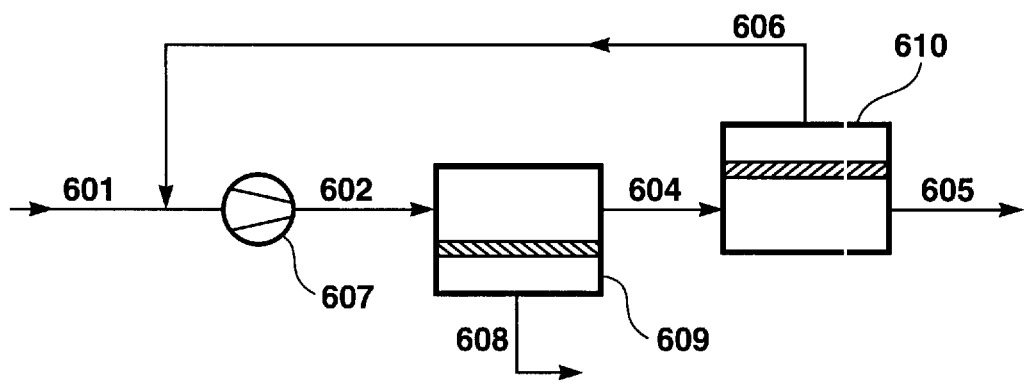
FIG. 6 is a schematic drawing of a two-step membrane separation unit and process.

Calculations were performed as in Example 20, except using a two-step process, wherein the residue from the first membrane step becomes the feed to a second membrane step, as shown in FIG. 6. In this Figure, line 601 contains the overhead stream from the ethylene oxide absorber. This stream is combined with the recycle stream in line 606. The combined stream passes through compressor 607, and the compressed stream in line 602 enters the first membrane unit, 609. Ethylene and methane permeate the membrane and are withdrawn through line 608. The first residue stream, withdrawn through line 604, is fed to the second membrane unit, 610. The second ethylene permeate is withdrawn through line 606 and recycled upstream of the compressor unit for further treatment. The residue stream in line 605 is nearly depleted of ethylene.

The process parameters were set to yield 98.2% ethylene recovery, to correspond with the results obtained from the single-stage membrane unit calculation of Example 22, that is, the 91% stage-cut case. The results of the calculations are shown in Table 28.

TABLE 28

| Component/Parameter | Stream 601 | Stream 602 | Stream 603 | Stream 604 | Stream 608 | Stream 605 | Stream 606 |
|---|---|---|---|---|---|---|---|
| Mass Flow Rate (lb/h) | 400.6 | 400.6 | 619.9 | 290.5 | 329.3 | 71.2 | 219.3 |
| Flow Rate (scfm) | 100 | 100 | 158.5 | 76.0 | 82.6 | 17.4 | 58.6 |
| Temperature(°C.) | 25 | 207 | 378 | 378 | 378 | 377 | 377 |
| Pressure (psia) | 20 | 200 | 200 | 200 | 20 | 200 | 20 |
| Component (mol %) | | | | | | | |
| Ethylene | 28.0 | 28.0 | 22.3 | 10.0 | 33.7 | 1.0 | 12.7 |
| Oxygen | 6.0 | 6.0 | 6.7 | 9.1 | 4.4 | 13.6 | 7.8 |
| Carbon Dioxide | 3.5 | 3.5 | 2.6 | 0.7 | 4.2 | 0.03 | 0.9 |
| Nitrogen | 2.0 | 2.0 | 1.9 | 3.2 | 0.7 | 8.4 | 1.7 |
| Argon | 10.0 | 10.0 | 11.1 | 15.0 | 7.6 | 21.6 | 13.1 |
| Methane | 50.5 | 50.5 | 55.4 | 61.9 | 49.5 | 55.4 | 63.8 |

Membrane Area: 19 m² (10 + 9)

The ethylene loss and ethylene recovery with the two-step process are shown in Table 29. These results are compared to the loss and recovery results obtained with a one-step membrane unit and no membrane unit. A normalizing factor was applied to the membrane area, so that in all cases the removal/recovery calculations could be compared on the basis of a vent stream that will release 10 scfm of argon.

TABLE 29

| Component | Ethylene | Oxygen | Carbon Dioxide | Nitrogen | Argon | Methane |
|---|---|---|---|---|---|---|
| Concentration in vent stream (mol %) | 1.0 | 13.6 | 0.03 | 8.4 | 21.6 | 55.4 |
| Moles lost/mole of argon vented (Two-Step) | 0.05 | 0.63 | 0.001 | 0.39 | 1.0 | 2.56 |
| Moles lost/mole of argon vented (One-Step) | 0.05 | 0.63 | 0.001 | 0.49 | 1.0 | 2.46 |
| Moles lost/mole of argon vented (No membrane) | 2.8 | 0.6 | 0.35 | 0.2 | 1.0 | 5.05 |
| Removal/Recovery compared to No membrane (%) | 98.2 | (5) | 99.7 | (95) | — | 49.3 |

Membrane Area: 53 m² (26.4 + 26.6)
Horsepower: 111.4 (Theoretical = 65.7 + Vent Compressor = 45.7)

Example 25

Figure 7:
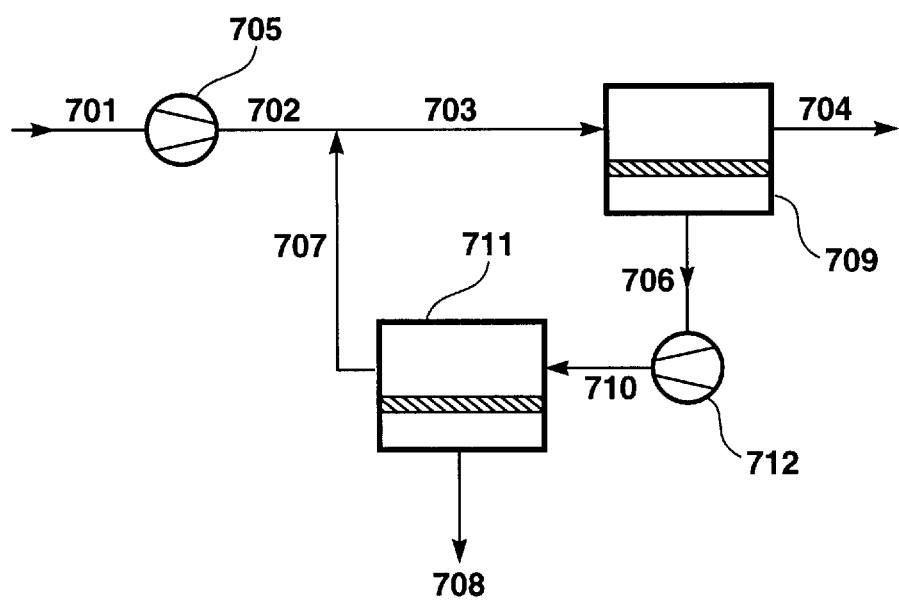
FIG. 7 is a schematic drawing of a two-stage membrane separation unit and process.

Calculations were performed as in Example 20, except using a two-stage process, wherein the permeate from the first membrane stage becomes the feed to a second membrane stage, as shown in FIG. 7. In this Figure, line 701 carries the overhead stream from the ethylene oxide absorber through compressor 705. The compressed stream in line 702 mixes with the recycled stream in line 707. This combined stream in line 703 enters the first membrane unit, 709, where ethylene and methane permeate the membrane and are withdrawn through line 706. This first permeate stream is recompressed in compressor 712, and fed via line 710 to the second membrane unit, 711. The second permeate is withdrawn through line 708. The second residue stream is withdrawn in line 707 and recycled upstream of the first membrane unit for further treatment. The first residue stream is vented via line 704.

As in Example 24, the process parameters were set to yield 98.2% ethylene recovery, to correspond with the single-stage calculation of Example 22. The results of the calculations are shown in Table 30.

TABLE 30

| Component/Parameter | Stream 701 | Stream 703 | Stream 704 | Stream 706 | Stream 710 | Stream 707 | Stream 708 |
|---|---|---|---|---|---|---|---|
| Mass Flow Rate (lb/h) | 400.6 | 1,258 | 135.0 | 1,123 | 1,123 | 856.7 | 266.2 |
| Flow Rate (scfm) | 100 | 330.3 | 34.3 | 296.0 | 296.0 | 230.1 | 65.9 |
| Temperature(°C.) | 25 | 84 | 18 | 18 | 25 | 23 | 23 |
| Pressure (psia) | 20 | 200 | 200 | 20 | 200 | 200 | 20 |
| Component (mol %) | | | | | | | |
| Ethylene | 28.0 | 22.4 | 1.0 | 24.9 | 24.9 | 20.0 | 42.0 |
| Oxygen | 6.0 | 5.8 | 12.4 | 5.0 | 5.0 | 5.7 | 2.7 |
| Carbon Dioxide | 3.5 | 2.3 | 0.02 | 2.6 | 2.6 | 1.8 | 5.3 |
| Nitrogen | 2.0 | 1.2 | 5.5 | 0.7 | 0.7 | 0.8 | 0.2 |
| Argon | 10.0 | 9.8 | 20.0 | 8.6 | 8.6 | 9.7 | 4.8 |
| Methane | 50.5 | 58.5 | 61.1 | 58.2 | 58.2 | 62.0 | 45.0 |

Membrane Area: 46 m$^2$ (39 + 7)

The ethylene loss and ethylene recovery with the two-stage process are shown in Table 31. These results are compared to the loss and recovery results obtained with a one-stage membrane unit and no membrane unit. A normalizing factor was applied to the membrane area, so that in all cases the removal/recovery calculations could be compared on the basis of a vent stream that will release 10 scfm of argon.

TABLE 31

| Component | Ethylene | Oxygen | Carbon Dioxide | Nitrogen | Argon | Methane |
|---|---|---|---|---|---|---|
| Concentration in vent stream (mol %) | 1.0 | 12.4 | 0.02 | 5.5 | 20.0 | 61.1 |
| Moles lost/mole of argon vented (Two-Stage) | 0.05 | 0.62 | 0.001 | 0.28 | 1.0 | 3.06 |
| Moles lost/mole of argon vented (One-Stage) | 0.05 | 0.63 | 0.001 | 0.49 | 1.0 | 2.46 |
| Moles lost/mole of argon vented (No membrane) | 2.8 | 0.6 | 0.35 | 0.2 | 1.0 | 5.05 |
| Removal/Recovery compared to No membrane (%) | 98.2 | (3.3) | 99.7 | (40) | — | 39.4 |

Membrane Area: 68.4 m$^2$ (58.2 + 10.2)
Horsepower: 107.9 (Theoretical 87.9 + Vent Compressor = 20.0)

We claim:

1. A process for producing ethylene oxide, comprising the following steps:

(a) reacting ethylene and oxygen in a reactor to form ethylene oxide;

(b) withdrawing from said reactor a product stream comprising ethylene oxide, ethylene and argon;

(c) removing at least a portion of said ethylene oxide from said product stream to form a non-product stream;

(d) providing a membrane having a feed side and a permeate side, and being selectively permeable to ethylene over argon;

(e) passing at least a portion of said non-product stream across said feed side under conditions in which there is a pressure drop from said feed side to said permeate side;

(f) withdrawing from said feed side an argon-rich purge stream enriched in argon and depleted in ethylene compared with said non-product stream;

(g) withdrawing from said permeate side an ethylene-rich permeate stream enriched in ethylene and depleted in argon compared with said non-product stream;

(h) recirculating at least a portion of said ethylene-rich permeate stream to said reactor; said process being characterized by a stage-cut between said ethylene-rich permeate stream and said non-product stream of at least about 30%.

2. The process of claim 1, wherein said membrane comprises a rubbery polymer.

3. The process of claim 1, wherein said membrane comprises silicone rubber.

4. The process of claim 1, :wherein said membrane has an ethylene/argon selectivity of at least about 4.

5. The process of claim 1, wherein said ethylene-rich permeate stream contains at least 50% of the ethylene that was present in said portion of said non-product stream.

6. The process of claim 1, wherein said ethylene-rich permeate stream contains at least 70% of the ethylene that was present in said portion of said non-product stream.

7. The process of claim 1, wherein said ethylene-rich permeate stream contains at least 90% of the ethylene that was present in said portion of said non-product stream.

8. The process of claim 1, wherein said non-product stream further comprises carbon dioxide and wherein at least a portion of said non-product stream is treated to remove carbon dioxide and then recirculated to said reactor.

9. The process of claim 1, wherein said non-product stream further comprises carbon dioxide and wherein said portion of said non-product stream is treated to at least partially remove carbon dioxide prior to carrying out said step (e).

10. A process for treating a purge stream from an ethylene oxide manufacturing process, said purge stream comprising ethylene and argon, said process comprising the following steps:
(a) providing a membrane having a feed side and a permeate side, and being selectively permeable to ethylene over argon;
(b) passing at least a portion of said purge stream across said feed side under conditions in which there is a pressure drop from said feed side to said permeate side;
(c) withdrawing from said feed side an argon-rich stream enriched in argon and depleted in ethylene compared with said purge stream;
(d) withdrawing from said permeate side an ethylene-rich permeate stream enriched in ethylene and depleted in argon compared with said purge stream;
(h) recirculating at least a portion of said ethylene-rich permeate stream to said ethylene oxide manufacturing process;

said process being characterized by a stage-cut between said ethylene-rich permeate stream and said purge stream of at least about 30%.

11. The process of claim 10, wherein said membrane comprises a rubbery polymer.

12. The process of claim 10, wherein said membrane comprises silicone rubber.

13. The process of claim 10, wherein said membrane has an ethylene/argon selectivity of at least about 4.

14. The process of claim 10, wherein said ethylene-rich permeate stream contains at least 50% of the ethylene that was present in said portion of said purge stream.

15. The process of claim 10, wherein said ethylene-rich permeate stream contains at least 70% of the ethylene that was present in said portion of said purge stream.

16. The process of claim 10, wherein said ethylene-rich permeate stream contains at least 90% of the ethylene that was present in said portion of said purge stream.

\* \* \* \* \*